US009968432B2

United States Patent
(12) United States Patent
Lagodzki et al.

(10) Patent No.: US 9,968,432 B2
(45) Date of Patent: May 15, 2018

(54) OCCLUSION DEVICE INCLUDING BUNDLE OF OCCLUSION WIRES HAVING PREFORMED SHAPES

(71) Applicant: Cook Medical Technologies LLC, Bloomington, IN (US)

(72) Inventors: Karol Lagodzki, Bloomington, IN (US); Tyler Turk, Greenwood, IN (US); Jeremy Schaeffer, Bloomington, IN (US); Trevor Plassman, Bloomington, IN (US); Elizabeth Anne Theobald, Bloomington, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 320 days.

(21) Appl. No.: 14/248,477

(22) Filed: Apr. 9, 2014

(65) Prior Publication Data

US 2015/0005807 A1 Jan. 1, 2015

Related U.S. Application Data

(66) Substitute for application No. 61/840,518, filed on Jun. 28, 2013.

(51) Int. Cl.

*A61M 29/00* (2006.01)
*A61F 2/01* (2006.01)
*A61B 17/12* (2006.01)

(52) U.S. Cl.

CPC .......... *A61F 2/01* (2013.01); *A61B 17/12145* (2013.01); *A61F 2002/011* (2013.01); *A61F 2002/016* (2013.01); *A61F 2002/018* (2013.01)

(58) Field of Classification Search

CPC .......... A61F 2002/016; A61F 2002/018; A61F 2/01; A61F 2/013; A61F 2002/011;

(Continued)

(56) References Cited

U.S. PATENT DOCUMENTS 3,374,788 A * 3/1968 Rosenthal ............ A61K 9/0039 128/840
5,669,933 A * 9/1997 Simon ...................... A61F 2/01 600/191

(Continued)

FOREIGN PATENT DOCUMENTS

| | | |
|---|---|---|
| EP | 0882428 | 12/1998 |
| EP | 1842490 | 10/2007 |
| WO | 0241753 | 5/2002 |
| WO | 2011084536 | 7/2011 |

*Primary Examiner* — Katrina Stransky
*Assistant Examiner* — Kankindi Rwego
(74) *Attorney, Agent, or Firm* — Liell & McNeil

(57) ABSTRACT

An occlusion system includes a delivery catheter having an elongate body defining a delivery lumen, and an occlusion device including a bundle of elongate occlusion wires configured for simultaneous delivery through the delivery lumen. At least a portion of each of the occlusion wires includes a shape memory material and has a preformed shape. The occlusion system includes a delivery configuration in which each of the occlusion wires is positioned within the delivery lumen, urged against the preformed shape, and substantially parallel to a longitudinal axis of the delivery lumen, and a post-deployment configuration in which each of the occlusion wires is released from the delivery lumen and conforms to the preformed shape. According to the preformed shape, each of the occlusion wires has a longitudinal segment remaining parallel to the longitudinal axis and a curved end providing an outward radial force with respect to the longitudinal axis.

18 Claims, 4 Drawing Sheets

(58) Field of Classification Search

CPC ...... A61F 6/20; A61F 6/22; A61F 6/18; A61F 6/146; A61F 6/148; A61F 2002/015; A61K 9/0036; A61B 17/12109; A61B 17/12113; A61B 17/12118; A61B 17/1214; A61B 17/12145; A61B 17/1215; A61B 17/12168; A61B 17/12172; A61B 17/12177; A61B 2017/12054; A61B 2017/12095; A61B 17/10; A61B 17/105; A61B 17/11; A61B 17/1114; A61B 17/1128; A61B 17/1146; A61B 17/115; A61B 17/1152; A61B 17/1155; A61B 17/12; A61B 17/12022; A61B 17/12027; A61B 17/12031; A61B 17/12036; A61B 17/1204; A61B 17/12154; A61B 17/12163; A61B 2017/1103; A61B 2017/1107; A61B 2017/111; A61B 2017/1117; A61B 2017/1121; A61B 2017/1125; A61B 2017/1132; A61B 2017/1135; A61B 2017/1139; A61B 2017/1142; A61B 2017/1157; A61B 2017/1205; A61B 2017/12063; A61B 2017/12068

See application file for complete search history.

(56) References Cited

U.S. PATENT DOCUMENTS

| | | | | |
|---|---|---|---|---|
| 6,790,218 | B2 | 9/2004 | Jayaraman | |
| 8,361,104 | B2 | 1/2013 | Jones et al. | |
| 8,366,741 | B2 | 2/2013 | Chin et al. | |
| 2003/0139819 | A1* | 7/2003 | Beer | A61B 17/0057 623/23.71 |
| 2006/0015137 | A1* | 1/2006 | WasDyke | A61F 2/01 606/200 |
| 2006/0116713 | A1 | 6/2006 | Sepetka et al. | |
| 2006/0155303 | A1* | 7/2006 | Konya | A61B 17/12022 606/108 |
| 2006/0203769 | A1* | 9/2006 | Saholt | A61F 2/01 370/329 |
| 2007/0255222 | A1* | 11/2007 | Li | A61J 15/0015 604/174 |
| 2008/0281350 | A1 | 11/2008 | Sepetka et al. | |
| 2009/0062838 | A1* | 3/2009 | Brumleve | A61B 17/12022 606/198 |
| 2012/0046687 | A1* | 2/2012 | Trommeter | A61B 17/12022 606/200 |

* cited by examiner

OCCLUSION DEVICE INCLUDING BUNDLE OF OCCLUSION WIRES HAVING PREFORMED SHAPES

TECHNICAL FIELD

The present disclosure relates generally to an occlusion device including a bundle of occlusion wires having preformed shapes, and more particularly to preformed shapes in which each of the occlusion wires has a longitudinal segment remaining parallel to a longitudinal delivery axis and a curved end providing an outward radial force with respect to the longitudinal delivery axis.

BACKGROUND

Embolization is a minimally invasive procedure that involves the selective occlusion of a vascular structure using one or more embolic devices. Typically, the embolic devices are positioned to reduce or restrict the blood supply to an arteriovenous malformation or other vascular lesion. Conventional embolic devices include embolic coils, which are typically delivered sequentially through a catheter and released at a treatment site. Alternatively, single device occlusion may be achieved using a vascular plug. A vascular plug typically includes an expandable mesh structure that is particularly suited for the occlusion of larger vascular structures. Once the embolic device is released or deployed at the treatment site, blood flow is restricted and clot formation occurs. While these embolic devices may prove effective for certain applications, both types of devices suffer drawbacks. For example, embolic coils may require a lengthy deployment time and may risk becoming dislodged and/or migrating. Drawbacks relating to the vascular plug relate to acute and chronic occlusion and may include, for example, a relatively long time to effect occlusion and the requirement for a relatively large delivery device.

International publication number WO 2011/084536 teaches a multi-fiber shape memory occlusion device that includes a plurality of coiled members. The coiled members are constrained in a pre-deployed state as a plurality of elongate members, and are reverted to preformed shapes to form a plurality of attached coiled members. In particular, as the fibers deploy and regain their memory shape, the fibers expand, coil, and form a coil pack. The resulting complex coil mass may be positioned, for example, within an aneurysm for restricting flow thereto.

The present disclosure is directed toward one or more of the problems or issues set forth above.

SUMMARY OF THE DISCLOSURE

In one aspect, an occlusion system includes a delivery catheter having an elongate body defining a delivery lumen, and an occlusion device including a bundle of elongate occlusion wires configured for simultaneous delivery through the delivery lumen. At least a portion of each of the elongate occlusion wires includes a shape memory material and has a preformed shape. The occlusion system includes a delivery configuration in which each of the elongate occlusion wires is positioned within the delivery lumen, urged against the preformed shape, and substantially parallel to a longitudinal axis of the delivery lumen. The occlusion system also includes a post-deployment configuration in which each of the elongate occlusion wires is released from the delivery lumen and conforms to the preformed shape. According to the preformed shape, each of the elongate occlusion wires has a longitudinal segment remaining parallel to the longitudinal axis and a curved end providing an outward radial force with respect to the longitudinal axis.

In another aspect, an occlusion device includes a bundle of elongate occlusion wires. At least a portion of each of the elongate occlusion wires includes a shape memory material and has a preformed shape. The occlusion device includes a delivery configuration in which each of the elongate occlusion wires is urged against the preformed shape and is substantially parallel to a longitudinal delivery axis, and a post-deployment configuration in which each of the elongate occlusion wires conforms to the preformed shape. According to the preformed shape, each of the elongate occlusion wires has a longitudinal segment remaining parallel to the longitudinal delivery axis and a curved end providing an outward radial force with respect to the longitudinal delivery axis.

In another aspect, a method of operating an occlusion system is provided. The occlusion system includes a delivery catheter having an elongate body defining a delivery lumen and an occlusion device including a bundle of elongate occlusion wires. At least a portion of each of the elongate occlusion wires includes a shape memory material and has a preformed shape. The method includes a step of advancing the elongate occlusion wires simultaneously through the delivery lumen of the delivery catheter to a target site in a delivery configuration of the occlusion system in which each of the elongate occlusion wires is urged against the preformed shape and is substantially parallel to a longitudinal axis of the delivery lumen. The method also includes transitioning the occlusion system from the delivery configuration to a post-deployment configuration in which each of the elongate occlusion wires is released from the delivery lumen and conforms to the preformed shape. According to the preformed shape, each of the elongate occlusion wires has a longitudinal segment remaining parallel to the longitudinal axis and a curved end providing an outward radial force with respect to the longitudinal axis. The occlusion device is anchored at the target site using the outward radial force of the curved end of each of the elongate occlusion wires.

DETAILED DESCRIPTION

Figure 1:
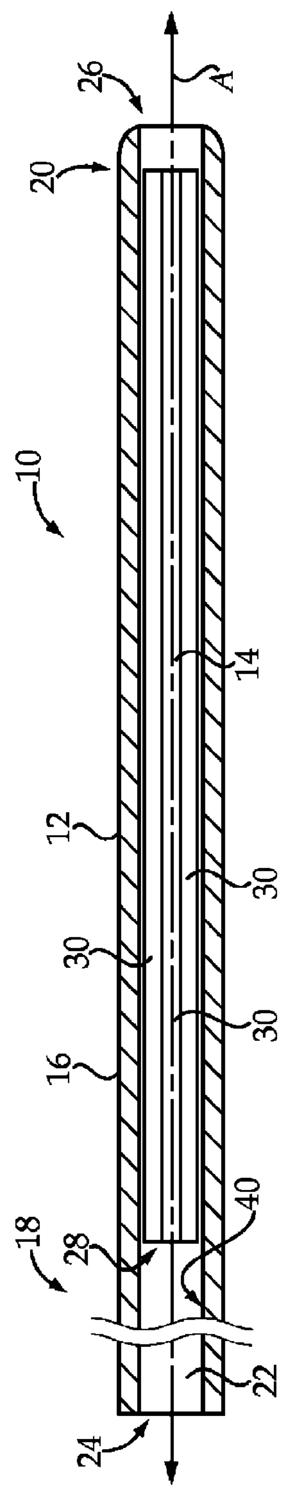
FIG. 1 is a partially sectioned side diagrammatic view of an occlusion system, shown in a delivery configuration, according to one embodiment of the present disclosure.

Referring to FIG. 1, there is shown an occlusion system 10 according to one embodiment of the present disclosure. The occlusion system 10 may include a number of components, which, according to some embodiments, may be provided within a sterile, tear open package, as is known in the art. In performing an embolization procedure on a patient, the components of the occlusion system 10 and additional components may be used, depending on the specifics of the procedure to be performed. As should be appreciated, however, components of the occlusion system 10 might be separately packaged and/or the occlusion system 10 might also include components in addition to those shown, including components routinely used in percutaneous vascular procedures.

The occlusion system 10 generally includes a delivery catheter 12 and an occlusion device 14. The delivery catheter 12 may include an elongate tubular body 16 having a proximal end 18 and a distal end 20. The elongate tubular body 16 may be made from any common medical tube material, such as, for example, polytetrafluoroethylene (PTFE), high density polyethylene (HDPE), nylon, polyetheretherketone (PEEK), or any vinyl, plastic, rubber, or silicone, and may exhibit both stiffness, or firmness, and flexibility. Materials as well as dimensions may vary depending on the particular application. In the present disclosure, “proximal” will be used to refer to the end of a component or feature that is closest to a clinician, while “distal” is used to refer to a component or feature that is farthest away from the clinician. Such meanings are consistent with conventional use of the terms and, as such, should be understood by those skilled in the art.

The elongate tubular body 16 may define a delivery lumen 22 extending from a proximal opening 24 to a distal opening 26. Although only one lumen, i.e., the delivery lumen 22, is shown, it should be appreciated that the delivery catheter 12 may include alternative numbers of lumens, such as, for example, two or three lumens. Although the delivery lumen 22 may be used for delivery of the occlusion device 14 and also as a wire guide lumen, it should be appreciated that a wire guide lumen separate from the delivery lumen 22 may be provided in some alternative embodiments. Delivery catheters, such as delivery catheter 12, are known and, thus, will not be discussed herein in greater detail. However, it should be appreciated that the occlusion system 10 may be used with, or may include, any of a variety of known delivery catheters or devices.

Figure 2:
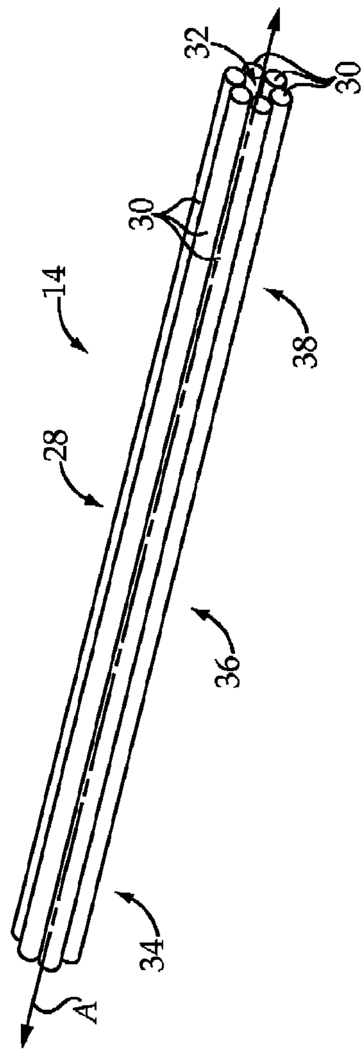
FIG. 2 is a perspective view of an occlusion device for use with the occlusion system of FIG. 1, shown according to the delivery configuration and defining a longitudinal central opening.

The occlusion device 14 includes a bundle 28 of elongate occlusion wires 30 configured for simultaneous delivery through the delivery lumen 22. Preferably, the occlusion device 14 includes at least six elongate occlusion wires 30, as shown in the view of FIG. 2, but any number of elongate occlusion wires 30 is contemplated. For example, some embodiments may include up to eighteen elongate occlusion wires 30. The “bundle” 28, as used herein, refers to a set or collection of elongate occlusion wires 30 that will typically be attached together to form a desired arrangement. For example, the elongate occlusion wires 30 may be attached together using any known attachment means, including, for example, welds, solder, adhesive, tape, shrink-wrap, and/or attachment means discussed below. According to one arrangement, and as shown in FIG. 2, the elongate occlusion wires 30 of the bundle 28 may be arranged to define a longitudinal central opening 32 configured for receiving a wire guide. By arranging the bundle 28 to accommodate a wire guide, a single lumen delivery catheter 12 may be used and a small delivery profile may be maintained.

The elongate occlusion wires 30 may be similar to one another with respect to materials, dimensions, and/or configurations, or may be different. However, according to all embodiments, each of the elongate occlusion wires 30 has a preformed shape and at least a portion of each of the elongate occlusion wires 30 includes a shape memory material. Although the lengths of each segment may vary, each of elongate occlusion wires 30 may be described as generally including a proximal segment 34, a central longitudinal segment 36, and a distal segment 38. As will be described below, at least one of the proximal segment 34, central longitudinal segment 36, and distal segment 38 may, according to the preformed shape, include a non-linear curl and may be made from a shape memory material. Shape memory materials are known any may include a metal alloy, such as nitinol, or a non-metal alloy, such as a shape memory polymer. Any material exhibiting known shape memory functionality, which includes the ability of a material to temporarily deform and recover its original, preformed shape after application of an external stimulus, may be used.

The occlusion device 14 or, more specifically, the occlusion system 10 is shown in FIG. 1 (and in FIG. 2) in a delivery configuration in which each of the elongate occlusion wires 30 is positioned within the delivery lumen 22, urged against the preformed shape using a wall 40 defining the delivery lumen 22, and is substantially linear and parallel with respect to a longitudinal axis A of the delivery lumen 22. In particular, the non-linear portion of the preformed shape may be urged into a substantially linear shape. The occlusion device 14, or occlusion system 10, also includes a post-deployment configuration in which each of the elongate occlusion wires 30 is released from the delivery lumen 22 and conforms to the preformed shape, or original shape. According to the preformed shape, each of the elongate occlusion wires 30 has a longitudinal segment, such as the central longitudinal segment 36, remaining parallel to the longitudinal axis A and a curved or curled end, such as one or both of the proximal segment 34 and the distal segment 38, providing an outward radial force with respect to the longitudinal axis A.

Figure 3:
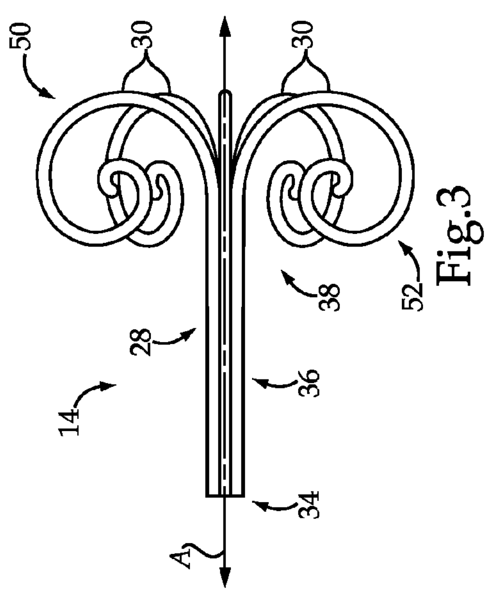
FIG. 3 is a side view of an exemplary occlusion device for use with the occlusion system of FIG. 1, shown in a post-deployment configuration.

For example, as shown in FIG. 3, the distal segment 38 of each of the elongate occlusion wires 30 may define a curved end 50. In particular, and according to the preformed shape, the proximal segment 34 and the central longitudinal segment 36 may remain parallel to the longitudinal axis A, while the curved end 50 provides an outward radial force with respect to the longitudinal axis A. Each curved end 50, as shown, may include a spiral 52 rotating outward relative to the longitudinal axis A. Since each of the elongate occlusion wires 30 is shown having a similar shape, the curved end 50 and spiral 52 are only referenced with respect to one of the elongate occlusion wires 30. Although the elongate occlusion wires 30 are shown having similar shapes and sizes, however, it should be appreciated that the occlusion wires 30 may differ with respect to size, shape, materials, and/or configuration.

Figure 4:
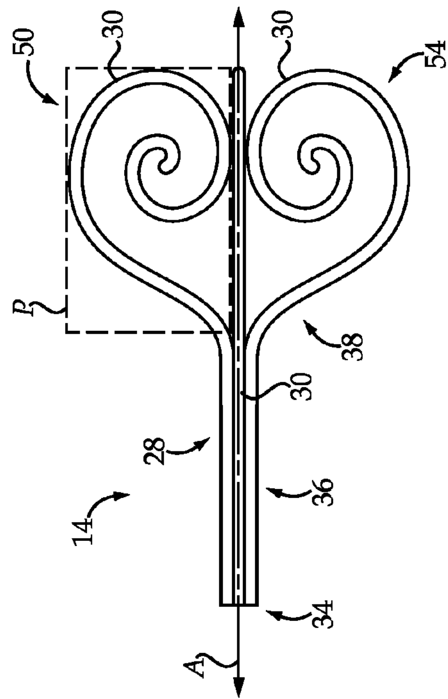
FIG. 4 is a side view of another exemplary occlusion device for use with the occlusion system of FIG. 1, shown in a post-deployment configuration.

Turning now to FIG. 4, another exemplary embodiment of the occlusion device 14 is shown. The exemplary embodiment of FIG. 4 is similar to the embodiment of FIG. 3, however, the curved end 50 of each of the elongate occlusion wires 30 includes a spiral 54 rotating inward relative to the longitudinal axis A. The curved end 50 of each of the elongate occlusion wires 30 of FIG. 4 also provides an outward radial force with respect to the longitudinal axis A, which will be used to anchor the occlusion device 14, as will be described below. According to any of the embodiments disclosed herein, and additional contemplated embodiments, each spiral 54, or other non-linear shape, may lie in a plane P parallel to the longitudinal axis A. According to some embodiments, the spirals 54 may be uniformly spaced about the longitudinal axis A to evenly distribute the outward radial force.

Figure 6:
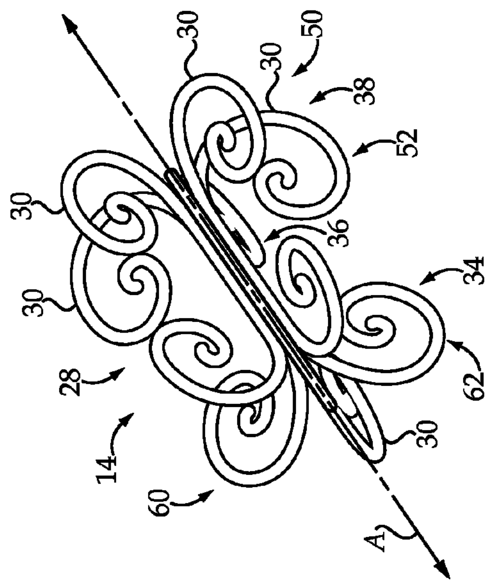
FIG. 6 is another exemplary occlusion device for use with the occlusion system of FIG. 1, shown in a post-deployment configuration.
Figure 5:
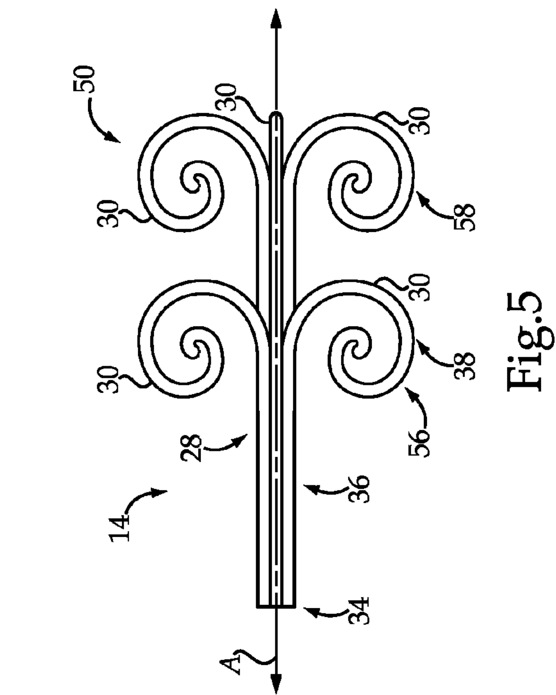
FIG. 5 is another exemplary occlusion device for use with the occlusion system of FIG. 1, shown in a post-deployment configuration.

According to another exemplary embodiment, the curved end 50 of at least one of the elongate occlusion wires 30 may be axially spaced along the longitudinal axis A from the curved end 50 of another of the elongate occlusion wires 30. In particular, and with reference to FIG. 5, at least one spiral 56 may be axially spaced from at least one other spiral 58 to define a staggered arrangement. As shown in FIG. 6, the proximal segment 34 of each of the elongate occlusion wires 30 may define an additional curved end 60. Specifically, according to the exemplary embodiment of FIG. 6, the distal segment 38 may define a first curved end 50, while the proximal segment 34 defines an additional curved end 60. The central longitudinal segment 36 may remain substantially parallel to the longitudinal axis A. As shown, each of the curved ends 50 and 60 may include spirals 52 and 62, respectively, rotating outward relative to the longitudinal axis A. Of course, different non-linear shapes providing outward radial forces may be substituted for one or both of spirals 52 and 62.

Figure 7:
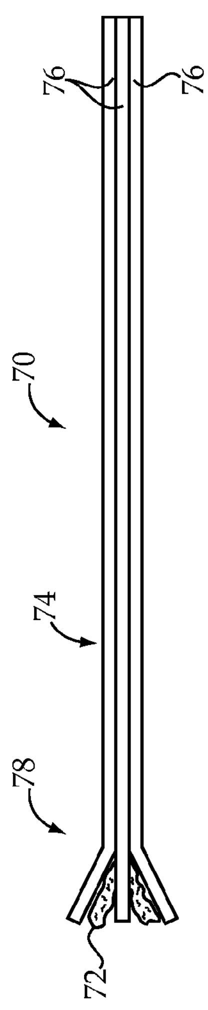
FIG. 7 is another exemplary occlusion device including a layer of occlusive material supported thereon, shown in a delivery configuration.
Figure 9:
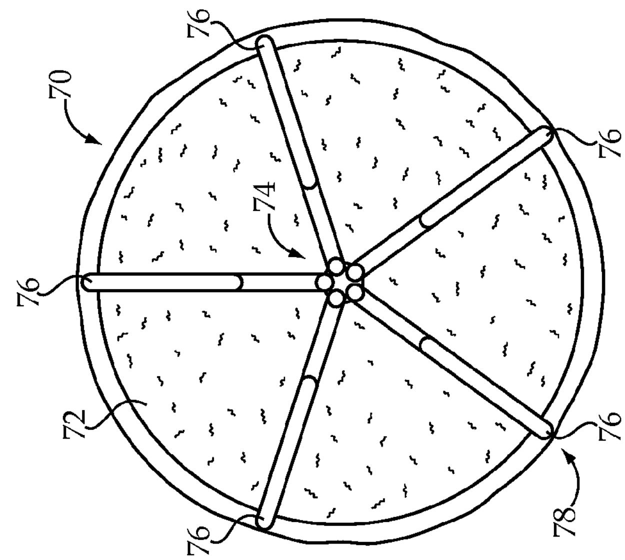
FIG. 9 is an end view of the occlusion device of FIGS. 7 and 8, shown in a post-deployment configuration.
Figure 8:
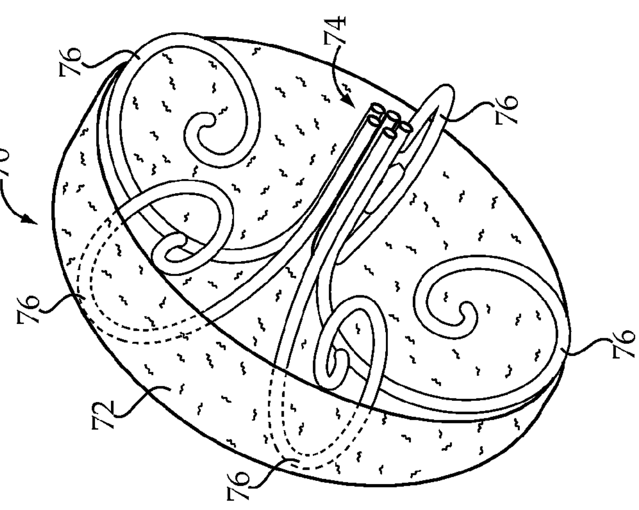
FIG. 8 is a perspective view of the occlusion device of FIG. 7, shown in a post-deployment configuration.

Referring to FIG. 7, an occlusion device 70 of the present disclosure may include a layer of occlusive material 72 supported thereon. The occlusive material 72 may be an elastic or non-elastic fibrous material, a wire mesh, a polymer mesh, or the like, provided to hasten occlusion and/or to secure a bundled configuration of the occlusion device 70. The occlusion device 70 of FIG. 7 may be similar to the occlusion device 14 described above and may generally include a bundle 74 of elongate occlusion wires 76. Each of the elongate occlusion wires 76 includes at least one end 78 having a non-linear shape, according to the preformed shape. According to the delivery configuration of FIG. 7, the end 78 is substantially urged against the preformed shape, but in the post-deployment configurations of FIGS. 8 and 9, the end 78 is permitted to conform to the preformed shape. As shown in FIGS. 7, 8, and 9, the layer of occlusive material 72 may be supported on the curved end 78, such as on an inward facing surface of each elongate occlusion wire 76 (in the delivery configuration). The layer of occlusive material 72 may be collapsed in the delivery configuration, as shown in FIG. 7, and expanded in the post-deployment configuration of FIGS. 8 and 9.

Figure 10:
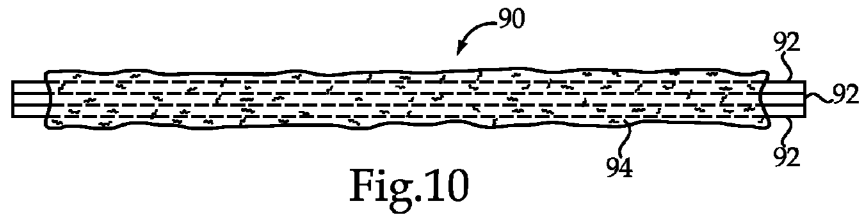
FIG. 10 is another exemplary occlusion device including a layer of occlusive material supported thereon, shown in a delivery configuration.
Figure 11:
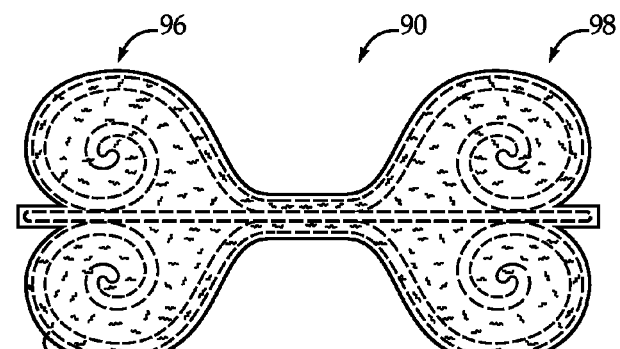
FIG. 11 is a side view of the occlusion device of FIG. 10, shown in a post-deployment configuration.

In FIG. 10, an occlusion device 90 is shown having a plurality of elongate occlusion wires 92. A layer of occlusive material 94 is supported on outer surfaces of the elongate occlusion wires 92 and extends a majority of a length of the elongate occlusion wires 92. Although not required, each of the elongate occlusion wires 92 includes a first curved end 96 and a second curved end 98. The occlusive material 94, and the occlusive material 72 of the previous Figs., may be porous or non-porous material suitable for further restricting blood flow. The occlusive material 72 or 94 may be used as the exclusive means for attaching the elongate occlusion wires 76 or 92, respectively, or the elongate occlusion wires 76 or 92 may be secured together using alternative fastening means. It should be appreciated that according to embodiments that include the occlusive material 94 extending the length of the occlusive device 90 and/or embodiments including two curved ends 96 and 98, additional flow restriction may be provided, resulting in more rapid occlusion. Occlusion devices 14, 70, and 90 may also include, or be coated with, drugs, such as, for example, oncolytic agents, coagulative agents, biologic agents, and analgesics.

INDUSTRIAL APPLICABILITY

Figure 12:
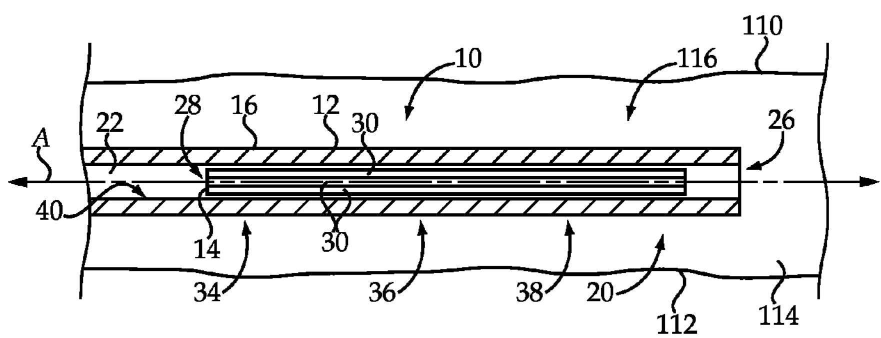
FIG. 12 is a side diagrammatic view of a vascular structure of a patient depicting one stage of an embolization procedure.

Turning now to FIG. 12, a percutaneous vascular procedure using the occlusion system 10 of FIG. 1 will be discussed with reference to a vascular structure 110 of a patient. Although a vascular structure 110 is shown, the present disclosure may be applicable to alternative bodily structures and lumens. The vascular structure 110, as should be appreciated, may include a vessel wall 112 defining a lumen 114. Although not shown, it should be appreciated that a clinician may first use an introducer to gain access to the vascular structure 110 in a known manner. Next, as shown in FIG. 12, the occlusion system 10 may be inserted through the introducer, over a standard wire guide, and into the vascular structure 110 such that the distal end 20 is appropriately positioned relative to a target site 116.

As shown, the elongate occlusion wires 30 are advanced simultaneously through the delivery lumen 22 of the delivery catheter 12 to the target site 116 in a delivery configuration of the occlusion system 10 in which each of the elongate occlusion wires 30 of the occlusion device 14 is urged against the preformed shape and is substantially parallel to a longitudinal axis A of the delivery lumen 22. Although not within the scope of the present disclosure, delivery means for delivering the occlusion device 14 to the target site 116 through the delivery catheter 12 may include a pusher wire, or other device, that may distally advance the occlusion device 14 relative to the delivery catheter 12, or hold the occlusion device 14 stationary while the delivery catheter 12 is proximally retracted. According to some embodiments, the occlusion device 14 may be restricted to the delivery configuration using a delivery sheath that is removed after the occlusion device 14 is released from the delivery catheter 12. However, various known deployment means may be used for delivering and deploying the occlusion device 14.

Figure 13:
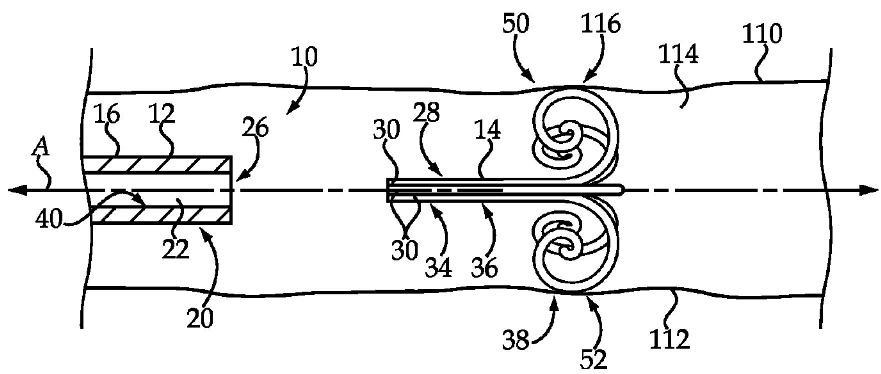
FIG. 13 is a side diagrammatic view of the vascular structure depicting another stage of an embolization procedure.

The occlusion system 10 is then transitioned from the delivery configuration to a post-deployment configuration, as shown in FIG. 13, in which each of the elongate occlusion wires 30 is released from the delivery lumen 22 and conforms to the preformed shape. According to the preformed shape, each of the elongate occlusion wires 30 has a longitudinal segment, such as the central longitudinal segment 36, remaining parallel to the longitudinal axis A and a curved end 50 providing an outward radial force with respect to the longitudinal axis A. In particular, the occlusion device 14 is anchored at the target site 116 using the outward radial force of the curved end 50 of each of the elongate occlusion wires 30. A desired orientation of the occlusion device 14 at the target site 116 may be maintained based on the preformed shape and the bundling, or attachment, of the elongate occlusion wires 30.

The occlusion devices disclosed herein provide means for quick and effective cessation of blood flow that is suitable for short-term and long-term occlusion of vascular structures. The occlusion devices have a relatively low delivery profile and may expand to accommodate vessels of a wide range of sizes. For example, the occlusion devices could be sized for delivery through a 0.038 inch catheter or a 0.020 inch microcatheter and could effect occlusion in vessels up to about 5 millimeters. Each of the elongate occlusion wires in a bundle is preformed to provide a predictable post-deployment shape of the occlusion device. Preformed shapes, such as curls or spirals, may be formed on one or both of the proximal and distal ends of the occlusion wires and may provide a continuous and evenly distributed outward radial anchoring force. Having preformed shapes that are on both ends of the elongate occlusion wires, or that are otherwise axially staggered, provides discrete stages of flow restriction that may improve and speed up occlusion. A layer of occlusive material supported on the bundle of occlusion wires may also improve occlusion and/or may assist in securing the bundle.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:

1. An occlusion system, comprising:

a delivery catheter having an elongate body defining a delivery lumen; and an occlusion device including a bundle of at least six elongate occlusion wires, with contiguous wires in contact with one another, and being configured for simultaneous delivery through the delivery lumen, wherein at least a portion of each of the elongate occlusion wires includes a shape memory material and has a preformed shape;

wherein the occlusion system includes: a delivery configuration in which each of the elongate occlusion wires is positioned within the delivery lumen, urged against the preformed shape, and substantially parallel to a longitudinal axis of the delivery lumen; and a post-deployment configuration in which each of the elongate occlusion wires is released from the delivery lumen and conforms to the preformed shape;

wherein, according to the preformed shape, each of the elongate occlusion wires has a longitudinal segment remaining parallel to the longitudinal axis and a curved end, which includes a spiral lying in a single plane parallel to the longitudinal axis, providing an outward radial force with respect to the longitudinal axis; and wherein a portion of the bundle defined by the longitudinal segments has an identical shape in the delivery configuration and the post-deployment configuration.

2. The occlusion system of claim 1, further including a layer of occlusive material supported on the curved end of each of the elongate occlusion wires, wherein the layer of occlusive material is collapsed to present a first area perpendicular to the longitudinal axis in the delivery configuration and expanded to present a second area perpendicular to the longitudinal axis, which is greater than the first area, in the post-deployment configuration.

3. The occlusion system of claim 1, wherein a distal segment, which is distal of the longitudinal segment, of each of the elongate occlusion wires defines the curved end.

4. The occlusion system of claim 3, wherein a proximal segment, which is proximal of the longitudinal segment, of each of the elongate occlusion wires defines an additional curved end, which includes an additional spiral lying in a single plane parallel to the longitudinal axis.

5. The occlusion system of claim 1, wherein the spiral, rotates inward relative to the longitudinal axis.

6. The occlusion system of claim 1, wherein the spiral, rotates outward relative to the longitudinal axis.

7. The occlusion system of claim 1, wherein the bundle of elongate occlusion wires defines a radially enclosed longitudinal central opening configured for receiving a wire guide.

8. An occlusion device, comprising:

a bundle of at least six elongate occlusion wires, with contiguous wires in contact with one another, wherein at least a portion of each of the elongate occlusion wires includes a shape memory material and has a preformed shape;

wherein the occlusion device includes: a delivery configuration in which each of the elongate occlusion wires is urged against the preformed shape and is substantially parallel to a longitudinal delivery axis; and a post-deployment configuration in which each of the elongate occlusion wires conforms to the preformed shape;

wherein, according to the preformed shape, each of the elongate occlusion wires has a longitudinal segment remaining parallel to the longitudinal delivery axis and a curved end, which includes a spiral lying in a single plane parallel to the longitudinal axis, providing an outward radial force with respect to the longitudinal delivery axis; and wherein a portion of the bundle defined by the longitudinal segments has an identical shape in the delivery configuration and the post-deployment configuration.

9. The occlusion device of claim 8, further including a layer of occlusive material supported on the curved end of each of the elongate occlusion wires, wherein the layer of occlusive material is collapsed to present a first area perpendicular to the longitudinal axis in the delivery configuration and expanded to present a second area perpendicular to the longitudinal axis, which is greater than the first area, in the post-deployment configuration.

10. The occlusion device of claim 8, wherein a distal segment, which is distal of the longitudinal segment, of each of the elongate occlusion wires defines the curved end.

11. The occlusion device of claim 10, wherein a proximal segment, which is proximal of the longitudinal segment, of each of the elongate occlusion wires defines an additional curved end, which includes an additional spiral lying in a single plane parallel to the longitudinal axis.

12. The occlusion device of claim 8, wherein the curved end of one of the elongate occlusion wires is a first spiral axially spaced along the longitudinal delivery axis from the curved end, which is a second spiral, of another of the elongate occlusion wires to define a staggered arrangement with the first spiral spaced apart from the second spiral along the longitudinal delivery axis.

13. The occlusion device of claim 8, wherein the curved end of each of the elongate occlusion wires includes a spiral, which terminates at an end of the respective wire, rotating inward relative to the longitudinal delivery axis.

14. The occlusion device of claim 8, wherein the curved end of each of the elongate occlusion wires includes a spiral, which terminates at an end of the respective wire, rotating outward relative to the longitudinal delivery axis.

15. The occlusion device of claim 8 wherein the bundle defines a longitudinal wire guide opening for receiving a wire guide.

16. A method of operating an occlusion system, the occlusion system including a delivery catheter having an elongate body defining a delivery lumen and an occlusion device including a bundle of at least six elongate occlusion wires, wherein at least a portion of each of the elongate occlusion wires includes a shape memory material and has a preformed shape, the method comprising steps of:

advancing the elongate occlusion wires simultaneously through the delivery lumen of the delivery catheter to a target site within a blood vessel in a delivery configuration of the occlusion system in which each of the elongate occlusion wires is urged against the preformed shape and is substantially parallel to a longitudinal axis of the delivery lumen;

transitioning the occlusion system from the delivery configuration to a post-deployment configuration in which each of the elongate occlusion wires is released from the delivery lumen and conforms to the preformed shape, wherein, according to the preformed shape, each of the elongate occlusion wires has a longitudinal segment remaining parallel to the longitudinal axis and a curved end, which includes a spiral lying in a single plane parallel to the longitudinal axis, providing an outward radial force with respect to the longitudinal axis;

anchoring the occlusion device at the target site using the outward radial force of the curved end of each of the elongate occlusion wires bearing against an inner wall of the blood vessel; and wherein a portion of the bundle defined by the longitudinal segments has an identical shape in the delivery configuration and the post-deployment configuration.

17. The method of claim 16, wherein the transitioning step includes moving a layer of occlusive material supported on the curved end of each of the elongate occlusion wires from a collapsed position to present a first area perpendicular to the longitudinal axis to an expanded position to present a second area perpendicular to the longitudinal axis, which is greater than the first area.

18. The method of claim 16 wherein the advancing step is accomplished by moving occlusion system over a wire guide received in a wire guide opening defined by the bundle.

* * * * *